United States Patent
Brown et al.

(10) Patent No.: US 10,111,786 B2
(45) Date of Patent: Oct. 30, 2018

(54) TAMPON APPLICATOR INCLUDING BEVELED PORTION

(71) Applicant: First Quality Hygienic, Inc., Great Neck, NY (US)

(72) Inventors: Shawn W. Brown, State College, PA (US); Daniel Wade Greenaway, Jersey Shore, PA (US); Christopher J. Graham, Lock Haven, PA (US); William J. Henry, Jersey Shore, PA (US); Willam M. Child, Lock Haven, PA (US)

(73) Assignee: First Quality Hygienic, Inc., Great Neck, NY (US)

( * ) Notice: Subject to any disclaimer, the term of this patent is extended or adjusted under 35 U.S.C. 154(b) by 478 days.

(21) Appl. No.: 14/683,258

(22) Filed: Apr. 10, 2015

(65) Prior Publication Data
US 2016/0296379 A1 Oct. 13, 2016

(51) Int. Cl.
*A61F 13/32* (2006.01)
*A61F 13/26* (2006.01)
*A61F 13/20* (2006.01)

(52) U.S. Cl.
CPC ........ *A61F 13/266* (2013.01); *A61F 13/2097* (2013.01); *A61F 13/263* (2013.01)

(58) Field of Classification Search
CPC ...... A61F 13/26; A61F 13/263; A61F 13/266; A61F 13/2097; A61F 15/003
See application file for complete search history.

(56) References Cited

U.S. PATENT DOCUMENTS

| | | |
|---|---|---|
| 3,124,134 A | 3/1964 | Gardner |
| 3,148,680 A | 9/1964 | Roberts et al. |
| 3,575,169 A | 4/1971 | Voss et al. |
| 3,895,634 A | 7/1975 | Berger et al. |
| D250,049 S | 10/1978 | Hite, Jr. |
| D250,663 S | 12/1978 | Koch et al. |
| 4,479,791 A | 10/1984 | Sprague |
| 4,536,178 A | 8/1985 | Lichstein et al. |
| 4,676,773 A | 6/1987 | Sheldon |
| 4,762,584 A | 8/1988 | Andreasen et al. |
| 4,846,802 A | 7/1989 | Sanders, III |
| 4,911,687 A * | 3/1990 | Stewart .................. A61F 13/34 604/11 |
| 5,256,048 A | 10/1993 | Jacobs et al. |
| 5,261,665 A | 11/1993 | Downey |
| 5,267,953 A | 12/1993 | Paul et al. |
| 5,389,067 A | 2/1995 | Rejai |

(Continued)

FOREIGN PATENT DOCUMENTS

| | | |
|---|---|---|
| EP | 2547304 | 1/2013 |
| WO | 2010046478 | 4/2010 |

*Primary Examiner* — Lynne Anderson
(74) *Attorney, Agent, or Firm* — Amster, Rothstein & Ebenstein LLP

(57) ABSTRACT

A tampon applicator assembly includes a barrel and a plunger. The barrel has a proximal opening, a distal opening, and a wall. The wall has an interior surface that defines a channel extending from the proximal opening to the distal opening, and includes a beveled portion that defines the proximal opening. The channel is configured to releasably retain a tampon. The plunger is disposed in the barrel and configured for slidable passage through the channel of the barrel.

14 Claims, 11 Drawing Sheets

(56) References Cited

U.S. PATENT DOCUMENTS

| | | |
|---|---|---|
| 5,389,068 A | 2/1995 | Keck |
| 5,395,308 A | 3/1995 | Fox et al. |
| 5,442,897 A | 8/1995 | Hinzmann et al. |
| 5,566,435 A | 10/1996 | Brown, Jr. |
| 5,571,540 A | 11/1996 | Weyenberg et al. |
| 5,614,230 A | 3/1997 | Weyenberg et al. |
| 5,634,248 A | 6/1997 | McNelis et al. |
| 5,788,910 A | 8/1998 | McNelis et al. |
| 5,800,751 A | 9/1998 | Barker |
| 5,891,081 A | 4/1999 | McNelis et al. |
| D415,565 S | 10/1999 | Hayes et al. |
| 5,986,000 A | 11/1999 | Williams et al. |
| 6,203,515 B1 | 3/2001 | Norquest et al. |
| 6,228,306 B1 | 5/2001 | Hoepft et al. |
| 6,254,565 B1 | 7/2001 | Williams et al. |
| 6,264,626 B1 | 7/2001 | Linares et al. |
| 6,322,531 B1 | 11/2001 | Cortese et al. |
| 6,368,000 B1 | 4/2002 | Park et al. |
| 6,368,442 B1 | 4/2002 | Linares et al. |
| 6,416,488 B1 | 7/2002 | Jackson et al. |
| 6,423,025 B1 | 7/2002 | Buzot |
| 6,464,920 B1 | 10/2002 | Kramer |
| 6,511,452 B1 | 1/2003 | Rejai et al. |
| 6,648,846 B2 | 11/2003 | Binner et al. |
| 6,652,477 B2 | 11/2003 | Karapasha et al. |
| 6,652,941 B1 | 11/2003 | Chadwick et al. |
| 6,673,032 B2 | 1/2004 | Buzot |
| 6,685,787 B2 | 2/2004 | Linares et al. |
| 6,706,942 B1 | 3/2004 | Zhao et al. |
| D492,033 S | 6/2004 | Jarman et al. |
| 6,749,788 B1 | 6/2004 | Holden et al. |
| 6,802,664 B2 | 10/2004 | Vial et al. |
| 6,821,468 B2 | 11/2004 | Stegmaier |
| 6,830,554 B2 | 12/2004 | Jackson et al. |
| 6,886,443 B2 | 5/2005 | Rejai |
| 6,890,324 B1 | 5/2005 | Jackson et al. |
| 6,919,038 B2 | 7/2005 | Meyer et al. |
| 6,923,789 B2 | 8/2005 | LeMay et al. |
| 6,932,805 B2 | 8/2005 | Kollwitz et al. |
| 6,936,211 B2 | 8/2005 | Binner et al. |
| 6,939,340 B1 | 9/2005 | Berges |
| 6,953,456 B2 | 10/2005 | Fuchs et al. |
| D514,700 S | 2/2006 | Weber et al. |
| D515,212 S | 2/2006 | Edgett et al. |
| D516,718 S | 3/2006 | Weber et al. |
| D517,210 S | 3/2006 | Weber et al. |
| D517,691 S | 3/2006 | Turchi et al. |
| 7,011,033 B2 | 3/2006 | Sargent, Jr. et al. |
| 7,081,110 B2 | 7/2006 | Karapasha |
| 7,083,756 B2 | 8/2006 | Strahler |
| 7,241,274 B2 | 7/2007 | Suga |
| D559,983 S | 1/2008 | Edgett et al. |
| D572,362 S | 7/2008 | Edgett et al. |
| D602,587 S | 10/2009 | Edgett et al. |
| D602,588 S | 10/2009 | VanDenBogart et al. |
| D612,940 S | 3/2010 | Edgett et al. |
| 7,704,242 B2 | 4/2010 | LeMay et al. |
| D615,202 S | 5/2010 | Edgett et al. |
| 7,727,208 B2 | 6/2010 | LeMay et al. |
| D620,592 S | 7/2010 | VanDenBogart et al. |
| D664,656 S | 7/2012 | Avigdor et al. |
| D665,499 S | 8/2012 | Avigdor et al. |
| 8,372,028 B2 | 2/2013 | Karapasha et al. |
| 8,458,882 B2 | 6/2013 | Mastalish et al. |
| 8,613,718 B2 | 12/2013 | Karapasha et al. |
| 8,728,022 B2 | 5/2014 | Tamburin |
| 8,943,658 B2 * | 2/2015 | Seki ................ A61F 13/263 |
| | | 156/556 |
| 2003/0070259 A1 | 4/2003 | Brown et al. |
| 2003/0073947 A1 | 4/2003 | Binner et al. |
| 2003/0073948 A1 | 4/2003 | Binner et al. |
| 2003/0163080 A1 | 8/2003 | LeMay et al. |
| 2003/0181844 A1 | 9/2003 | Bernard |
| 2003/0216680 A1 | 11/2003 | Binner et al. |
| 2004/0010220 A1 | 1/2004 | Miller et al. |
| 2004/0060138 A1 | 4/2004 | Pfenniger et al. |
| 2004/0199102 A1 | 10/2004 | LeMay et al. |
| 2005/0015041 A1 | 1/2005 | Karapasha |
| 2005/0177091 A1 | 8/2005 | Jarmon et al. |
| 2005/0260394 A1 | 11/2005 | Ajbani et al. |
| 2006/0135905 A1 | 6/2006 | Miller et al. |
| 2007/0156081 A1 | 7/2007 | Karapasha |
| 2007/0222109 A1 | 9/2007 | Pfenniger et al. |
| 2008/0033337 A1 | 2/2008 | Dougherty et al. |
| 2008/0119778 A1 | 5/2008 | Jorgensen et al. |
| 2008/0228128 A1 | 9/2008 | Karapasha |
| 2008/0255496 A1 | 10/2008 | Sargent et al. |
| 2009/0112148 A1 | 4/2009 | Morrow |
| 2010/0016780 A1 | 1/2010 | VanDenBogart et al. |
| 2010/0100028 A1 | 4/2010 | Gilbert |
| 2010/0164139 A1 | 7/2010 | LeMay et al. |
| 2010/0193386 A1 | 8/2010 | Loyd et al. |
| 2010/0204636 A1 | 8/2010 | LeMay et al. |
| 2010/0324467 A1 | 12/2010 | Hasse |
| 2010/0324468 A1 | 12/2010 | Gann |
| 2011/0140308 A1 | 6/2011 | Melvin |
| 2011/0144561 A1 | 6/2011 | Watanabe |
| 2011/0179612 A1 | 7/2011 | Takai |
| 2011/0190685 A1 | 8/2011 | Arora |
| 2011/0190686 A1 | 8/2011 | Hasse |
| 2011/0190687 A1 | 8/2011 | Slayton |
| 2011/0201992 A1 | 8/2011 | Smet |
| 2011/0245754 A1 | 10/2011 | Morrow |
| 2011/0270150 A1 | 11/2011 | Karapasha |
| 2011/0275977 A1 | 11/2011 | Watanabe |
| 2012/0016288 A1 | 1/2012 | Sargent |
| 2012/0059306 A1 | 3/2012 | Tamburin |
| 2012/0101424 A1 | 4/2012 | Watanabe |
| 2012/0220918 A1 | 8/2012 | Chaffringeon |
| 2013/0066254 A1 | 3/2013 | LeMay et al. |

\* cited by examiner

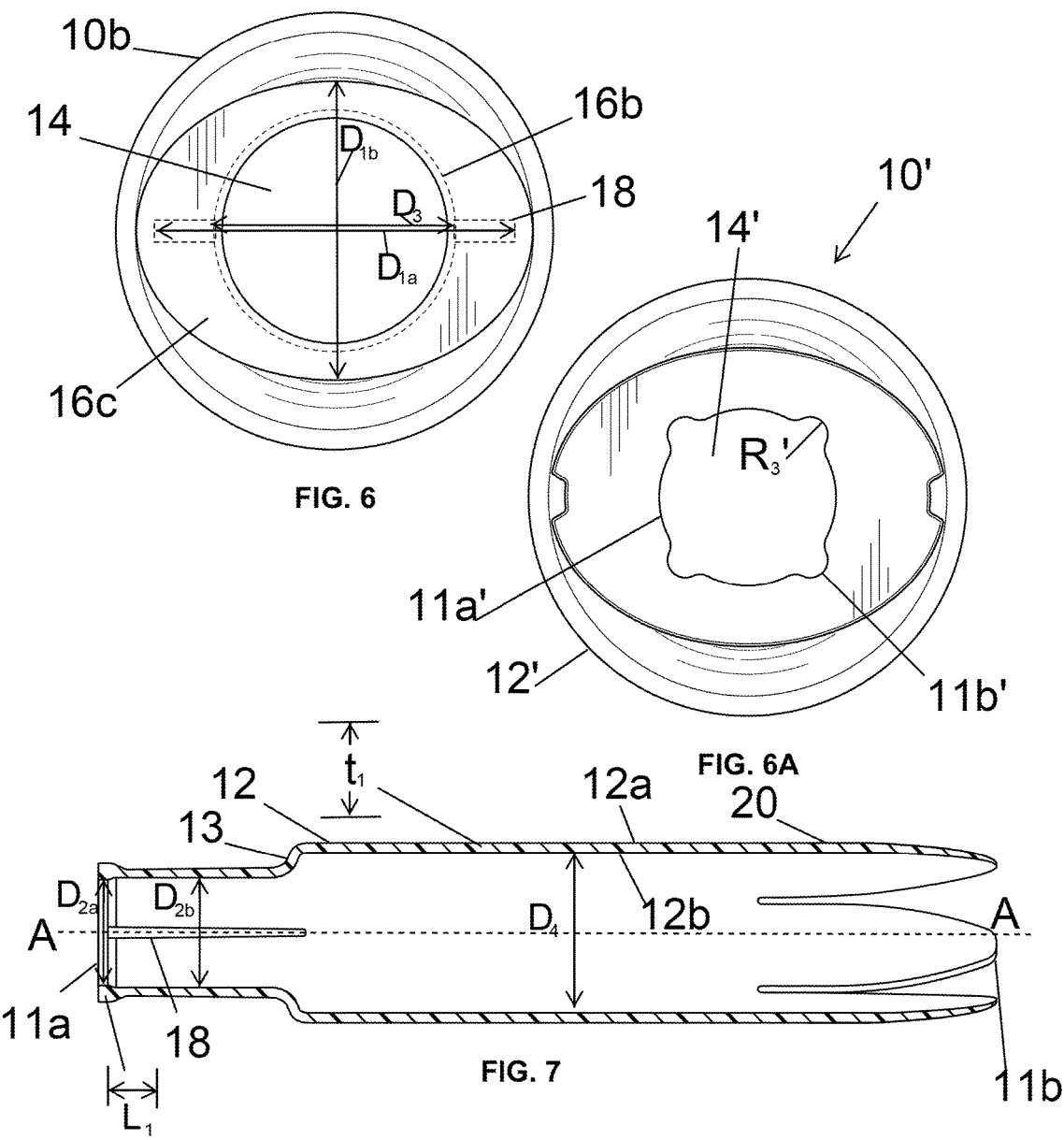

TAMPON APPLICATOR INCLUDING BEVELED PORTION

FIELD

The present invention is directed to a tampon applicator, and in particular, to a tampon applicator including a barrel having a beveled portion.

BACKGROUND

Tampon applicator assemblies may include a barrel configured to releasably retain a tampon and a plunger slidably movable within at least a portion of the barrel to push the tampon out of the barrel.

Tampon applicator assemblies are typically produced in high volumes due to their high commercial demand. Accordingly, it is desirable to develop efficient and cost-effective methods of producing tampon applicator assemblies.

SUMMARY

According to an exemplary embodiment of the present invention, a tampon applicator assembly comprises a barrel and a plunger. The barrel comprises a proximal opening, a distal opening, and a wall. The wall has an interior surface that defines a channel extending from the proximal opening to the distal opening, and includes a beveled portion that defines the proximal opening. The channel is configured to releasably retain a tampon. The plunger is disposed in the barrel and configured for slidable passage through the channel of the barrel.

In embodiments, a pair of interior ridges extend along the interior surface of the wall into the channel.

In embodiments, the pair of internal ridges is configured to align the plunger with the center of the channel as the plunger slides through the channel.

In embodiments, the pair of internal ridges is disposed along an elliptical proximal portion of the barrel defining a major diameter and a minor diameter.

In embodiments, the pair of internal ridges extends along the major diameter of the elliptical proximal portion.

In embodiments, the pair of internal ridges defines a diameter therebetween that is greater than or equal to the minor diameter of the channel.

In embodiments, the pair of interior ridges is spaced from the beveled portion.

In embodiments, the plunger includes a flared proximal end portion.

In embodiments, a proximal end portion of the plunger is deformable.

In embodiments, the beveled portion has a greater rigidity than a rigidity of the proximal portion of the plunger.

In embodiments, the beveled portion comprises a base defining a maximum diameter of the beveled portion and a collar defining a minimum diameter of the beveled portion.

In embodiments, the minimum diameter of the beveled portion is less than a diameter of a proximal portion of the plunger.

In embodiments, the proximal opening is circular.

In embodiments, the proximal opening includes one or more cutouts extending away from the channel.

In embodiments, the proximal opening includes two pairs of diametrically opposed cutouts extending away from the channel.

In embodiments, each of the cutouts is semi-circular.

In an exemplary embodiment, a method of assembling a tampon applicator assembly comprises providing a tampon applicator assembly that includes a barrel that includes a proximal opening, a distal opening, and a wall with an interior surface that defines a channel extending from the proximal opening to the distal opening, the wall comprising a beveled portion that defines the proximal opening, and a plunger disposed in the barrel and configured for slidable passage through the channel of the barrel. The method further comprises inserting the plunger into the distal opening of the barrel and proximally through the channel toward the beveled portion. The method further comprises moving the plunger along the beveled portion so that a portion of the plunger is deformed by the beveled portion.

In embodiments, the method further comprises moving the plunger through the proximal opening of the barrel so that the deformed portion of the plunger resiliently returns to an unstressed resting configuration.

BRIEF DESCRIPTION OF THE DRAWINGS

The features and advantages of the present invention will be more fully understood with reference to the following detailed description of illustrative embodiments of the present invention when taken in conjunction with the accompanying figures, wherein:

FIG. 6 is a bottom plan view of the barrel of the tampon applicator assembly of FIG. 1;

FIG. 6A is a bottom plan view of a barrel of a tampon applicator assembly according to an exemplary embodiment of the present disclosure;

FIG. 7 is a cross-sectional view taken along section line 7-7 of FIG. 3;

DETAILED DESCRIPTION OF EMBODIMENTS

In some tampon applicator assemblies, a plunger, barrel, and tampon are separately produced, assembled, and then packaged so that no additional assembly steps are required on the part of the user. Opposing ends of the plunger may be flared to prevent the plunger from separating from or being over-inserted through the barrel. Further, one flared end of the plunger presents a larger engagement surface for contacting a tampon in the barrel. However, the assembly of such tampon applicator assemblies requires a flared end of the plunger to be passed through a narrow opening of the barrel. One solution to this challenge involves configuring the barrel to deform a flared end of the plunger as it passes through the barrel.

As used herein, the term "proximal" refers to that portion of an object or component thereof that is closest to the point of contact with a controlling portion of a user's body, such as a finger or hand, during normal operation. As used herein, the term "distal" refers to that portion of an object or component thereof that is furthest from the point of contact with a controlling portion of a user's body, such as a finger or hand, during normal operation.

Figure 1:
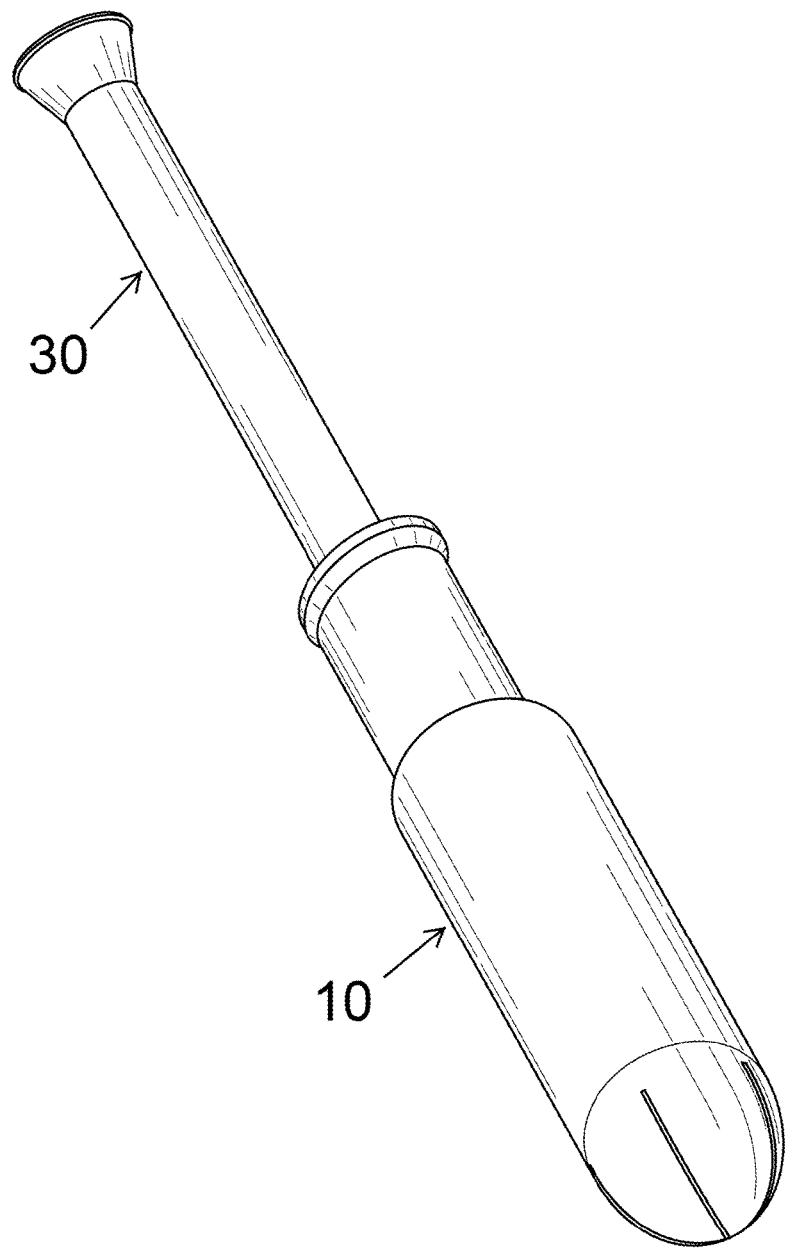
FIG. 1 is a perspective view of a tampon applicator assembly according to an exemplary embodiment of the present invention.

FIG. 1 is a perspective view of a tampon applicator assembly, generally designated by reference 100, according to an exemplary embodiment of the present invention. Tampon applicator assembly 100 includes a barrel 10 and a plunger 30. Barrel 10 and plunger 30 are configured to be inter-engaged so that tampon applicator assembly 100 can have a unitary structure, as shown. Barrel 10 and plunger 30 are configured to mechanically cooperate so that the plunger 30 causes a tampon to be pushed from the barrel 10 into the vaginal cavity of a user, as will be described further below. Each of barrel 10 and plunger 30 is formed of a suitable biocompatible material, such as a polymeric material or a composite material. Examples of such materials include polyolefins, biodegradable polymers such as polyvinyl alcohol and polyethylene oxide, or combinations thereof. In one preferred embodiment, the barrel and plunger are made of low density polyethylene.

Figure 2:
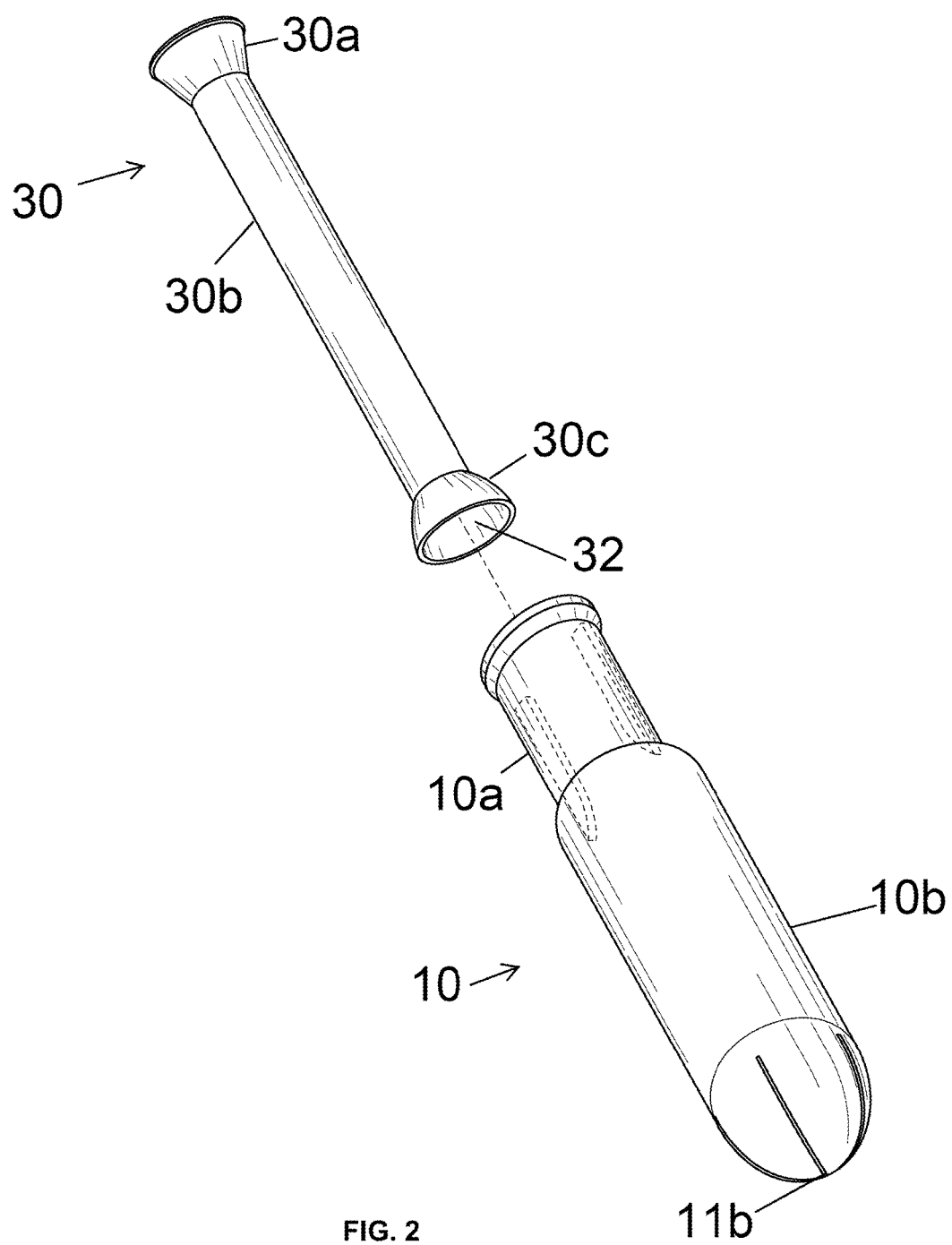
FIG. 2 is a perspective view of the tampon applicator assembly of FIG. 1, with its parts separated.
Figure 3:
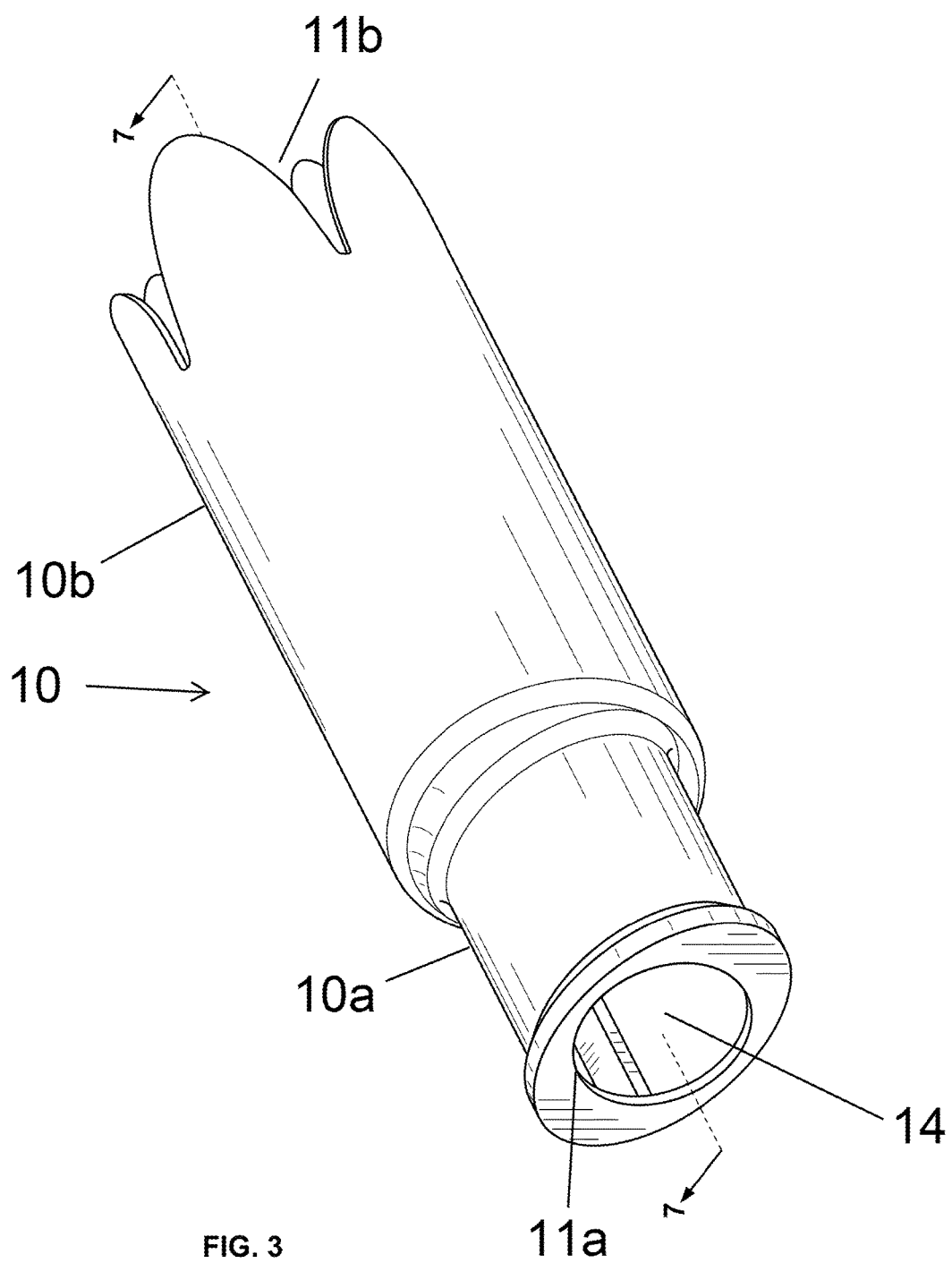
FIG. 3 is a perspective view of the barrel of the tampon applicator assembly of FIG. 1.
Figures 4, 5:
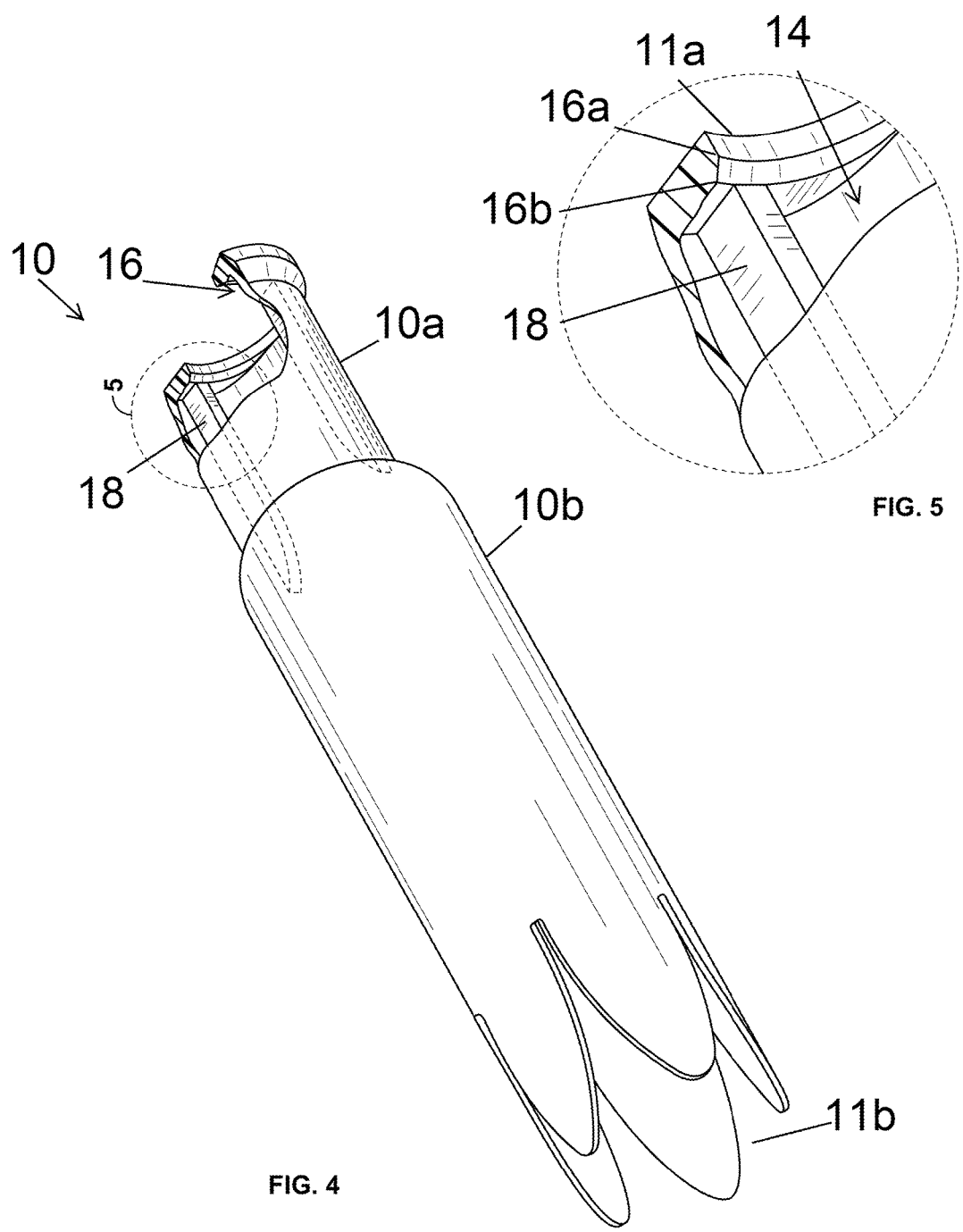
FIG. 4 is a perspective view of the barrel of the tampon applicator assembly of FIG. 1 with a portion of the barrel shown in breakaway.
FIG. 5 is an enlarged view of the area of detail identified in FIG. 4.

With reference to FIGS. 2 and 3, barrel 10 has a substantially elongate body that defines a proximal portion 10a, a distal portion 10b, a proximal opening 11a, and a distal opening 11b. A channel 14 is defined through the barrel 10 between proximal opening 11a and distal opening 11b.

Referring to FIG. 7, barrel 10 is formed by a generally cylindrical wall 12 having an outer surface 12b and an inner surface 12a. Wall 12 may define a thickness $t_1$ between the outer surface 12b and the inner surface 12a.

Proximal portion 10a of barrel 10 is configured for gripping by a user. In this regard, proximal portion 10a of barrel 10 has an ergonomic configuration suitable for manual engagement. As shown in FIG. 6, proximal portion 10a has an ovoid cross-sectional profile that defines a major diameter $D_{1a}$ and a minor diameter $D_{1b}$. In this regard, proximal portion 10a of barrel 10 may present a narrower profile than the remainder of barrel 10 so that the proximal portion 10b can be grasped, for example, between the thumb and middle finger of a user. In embodiments, proximal portion 10a of barrel may have any suitable configuration and/or cross-sectional profile, for example, circular, square, rectangular, triangular, pentagonal, or star-shaped, to name a few.

Turning to FIG. 6A, an exemplary embodiment of a barrel, generally designated 10', is shown in plan view. Barrel 10' includes a proximal portion 10a' that defines a proximal opening 11a' as shown. Proximal opening 11a' has a substantially circular profile with two pairs of diametrically opposed cutouts 11b' extending away from the interior channel 14' extending through barrel 10'. The diametrically opposed cutouts 11b' have a radius of curvature $R_3'$ such that cutouts 11b' have a semi-circular configuration. Cutouts 11b' increase the area defined by the circular portion of proximal opening 11a' of barrel 10', for example, so that a flared end of a plunger can be passed through proximal opening 11a'. Other portions of barrel 10', such as interior channel 14' and a wall 12' of barrel 10', may have the same shape as proximal opening 11a'. In embodiments, barrel 10' may include any number, shape, and/or dimension of cutouts 11b'.

With reference to FIGS. 4, 5, 6, and 7, barrel 10 includes a beveled portion 16 along the interior surface 12a of wall 12. Beveled portion 16 of wall 12 is positioned near the proximal opening 10a of barrel 10. In this regard, beveled portion 16 is a region of gradually reducing interior diameter of the wall 12 toward the proximal opening 11a of the barrel 10. Beveled portion 16 of wall 12 includes a circular base 16b with a diameter $D_{2b}$ defining the widest region of beveled portion 16, and tapers proximally toward a circular collar 16a with a diameter $D_{2a}$ defining the narrowest region along the beveled portion 16 of wall 12. Diameter $D_{2b}$ is the same as or less than to the minor diameter $D_{1b}$ of proximal portion 10a of barrel 10. An axial length $L_1$ may be defined between collars 16a, 16b along the proximal portion 10a of barrel 10. Collar 16a circumscribes the proximal opening 11a of barrel 10 so that the proximal opening 11a of barrel 10 has the same diameter $D_{2a}$. A pair of shoulders 16c extends between the interior surface 12a of wall 12 and collar 16a along the major diameter $D_{1a}$ of proximal portion 10a of barrel 10. In embodiments, the beveled portion 16 of wall 12 may have a different configuration, such as a non-linear and/or asymmetrical taper between base 16b and collar 16a.

According to at least one embodiment, a pair of internal ridges 18 extends from the interior surface 12a of wall 12 into channel 14 of barrel 10. Internal ridges 18 are aligned along the major diameter $D_{1a}$ of the proximal portion 10a of barrel 10 from the interior surface 12a of wall 12. As shown in FIG. 6, internal ridges 18 are diametrically opposed about the channel 14 along the proximal portion 10a of barrel 10 so that a diameter $D_3$ is defined between the internal ridges 18. Diameter $D_3$ may be greater than or equal to the diameter $D_{2b}$ of the base 16b of beveled portion 16 of wall 12. Internal ridges 18 have a rigid configuration so that internal ridges 18 engage and/or guide the movement of a plunger passing through channel 14, as will be described further below. In this regard, internal ridges 18 form a boundary about channel 14 so that an object approaching proximal portion 10a of barrel 10 through distal portion 10b of barrel 10 is urged into alignment with the channel 14 for passage therethrough. In embodiments, internal ridges 18 may extend along the entire length of proximal portion 10a, or may extend a distance greater than or less than the axial length of proximal portion 10a. In embodiments, barrel 10 may include any number of internal ridges 18, such as 1, 2, 3, 4, or 5, to name a few. In embodiments, barrel 10 may be devoid of internal ridges 18.

As described above, distal portion 10b of the barrel 10 releasably retains a tampon for placement in a user's body. Accordingly, distal portion 10b of barrel 10 defines a diameter $D_4$ that is greater than the minor diameter $D_{1b}$ of proximal portion 10a of barrel 10 so that a tampon can be disposed within the channel 14 along the distal portion 10b of barrel 10. Diameter $D_4$ may be greater than the major diameter $D_{1a}$ of the proximal portion 10a of barrel 10. Barrel 10 transitions between the proximal portion 10a and the distal portion 10b along a neck 13. In this regard, neck 13 defines a transition region of variable diameter along barrel 10. Internal ridges 18 may extend at least partially along neck 13.

A plurality of petals 20 is disposed about the distal opening 11b of the barrel 10 so that petals 20 define the distal opening 11b of barrel 10. Petals 20 are movable relative to the remainder of barrel 10 so that each of the petals 20 can transition between a first position and a second, radially outward position. Petals 20 have a complementary configuration so that adjacent petals 20 together form a symmetrical boundary about the distal opening 11b of barrel 10. Petals 20 may be monolithically formed with the remainder of barrel 10 so that petals 20 can flex with respect to the remainder of barrel 10. Each of the petals 20 is configured to move between and including 0 degrees and 135 degrees measured with respect to an axis A defined through channel 14. In embodiments, petals 20 may have a variety of configurations, for example, triangular, circular, planar, and/or curved, to name a few, and may be movably coupled with the remainder of barrel 10, for example, hingably attached or coupled along a perforation.

Referring to FIG. 2, plunger 30 is an elongate member that includes a stem 30b having a proximal flared end portion 30a and a distal flared end portion 30c. Plunger 30 has a tubular configuration such that proximal flared end portion 30a, stem 30b, and distal flared end portion 30c together define a passage 32 extending through plunger 30. Plunger 30 is sufficiently rigid to withstand axially compressive forces so that plunger 30 can transfer forces between a user and tampon disposed in the barrel 10.

Proximal flared end portion 30a of plunger 30 defines an outer diameter $D_5$ (FIG. 8E) that is greater than the diameter $D_{2a}$ of the collar 16a of beveled portion 16. As will be described further below, proximal flared end portion 30a is configured to deform under an applied force. In this regard, proximal flared end portion 30a is deformable under an applied force that does not cause deformation of the remainder of plunger 30. Proximal flared end portion 30a has a resilient configuration so that proximal flared end portion 30a tends to return toward its unstressed, flared condition. In embodiments, plunger 30 may have a different configuration, such as an asymmetrical shape, a non-circular cross-sectional profile and/or be solid along portions thereof.

Figure 8A:
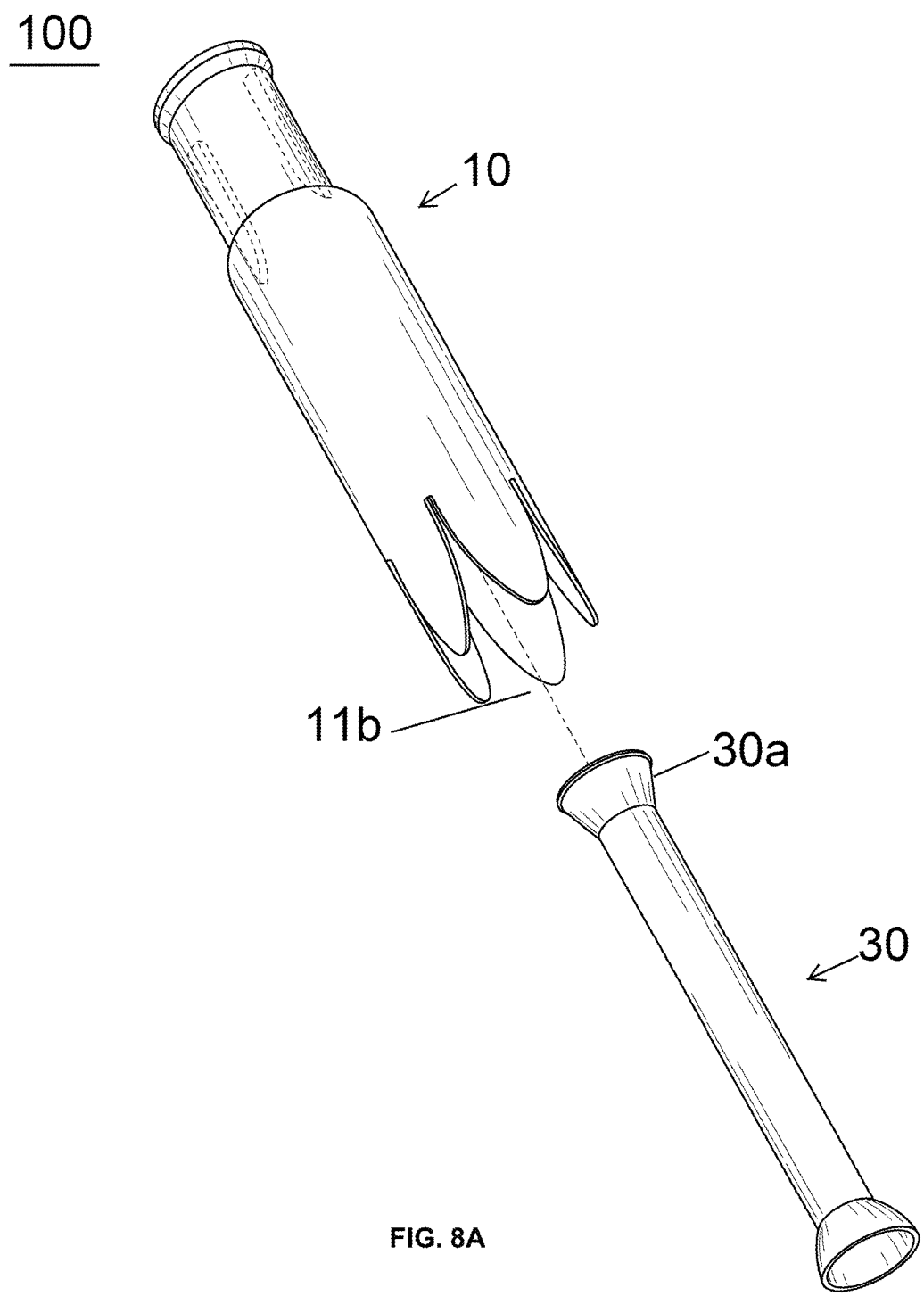
FIG. 8A is a first sequential assembly view of the tampon applicator assembly of FIG. 1.

Referring to FIGS. 8A-8E, a method of assembling tampon applicator assembly 100 will be described. With reference to FIG. 8A, barrel 10 and plunger 30 are arranged so that the proximal flared end portion 30a is aligned with and positioned for entry through the distal end 11b of barrel 10.

Figure 8B:
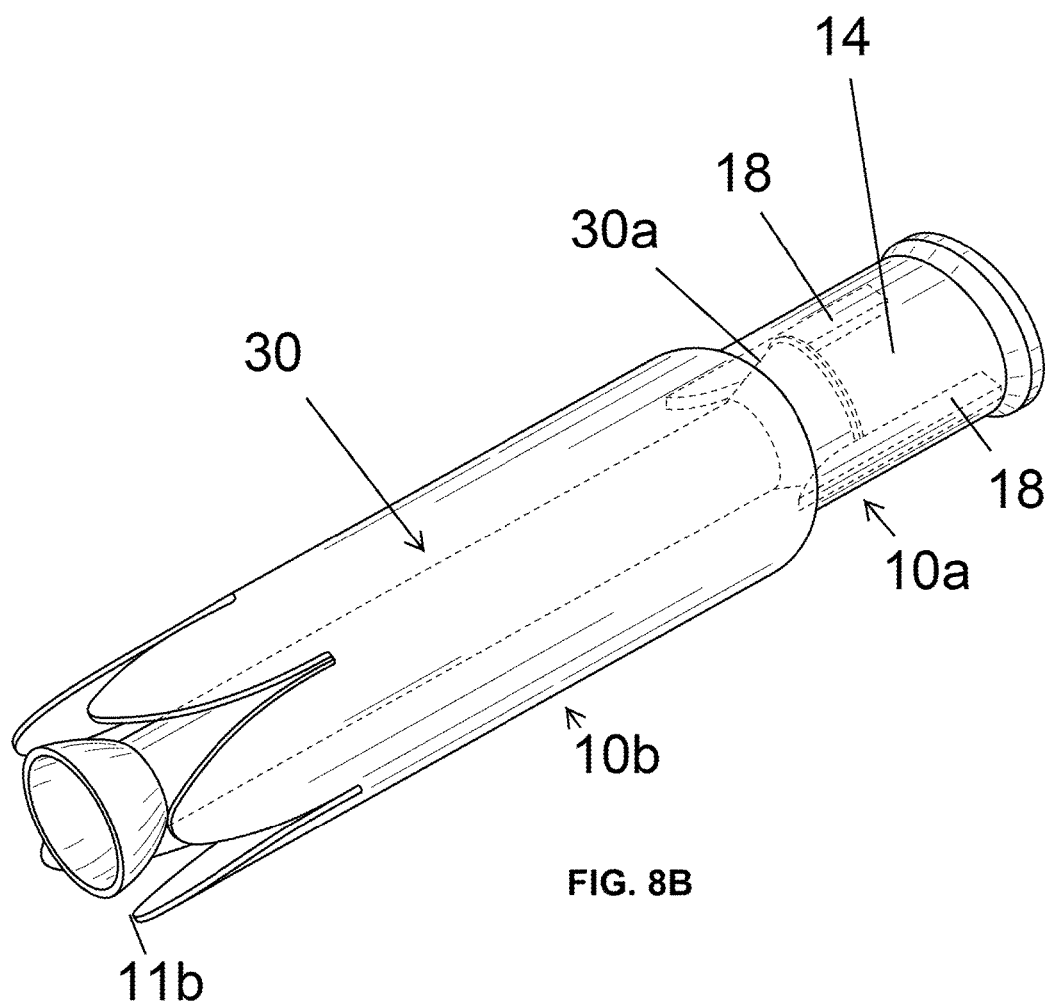
FIG. 8B is a second sequential assembly view of the tampon applicator assembly of FIG. 1.

With reference to FIG. 8B, plunger 30 is inserted through the distal end 11b and into the distal portion 10b of barrel 10. As the proximal flared end portion 30a of plunger 30 is moved further proximally and approaches the neck 13 of barrel 10, proximal flared end portion 30a engages internal ridges 18 so that internal ridges 18 guide the plunger 30 into alignment with the channel 14 as the plunger 30 moves into the proximal portion 10a of barrel 10. In this regard, internal ridges 18 inhibit plunger 30 from moving out of alignment with channel 14 as plunger 30 approaches, enters, and passes through proximal portion 10a of barrel 10.

Figure 8C:
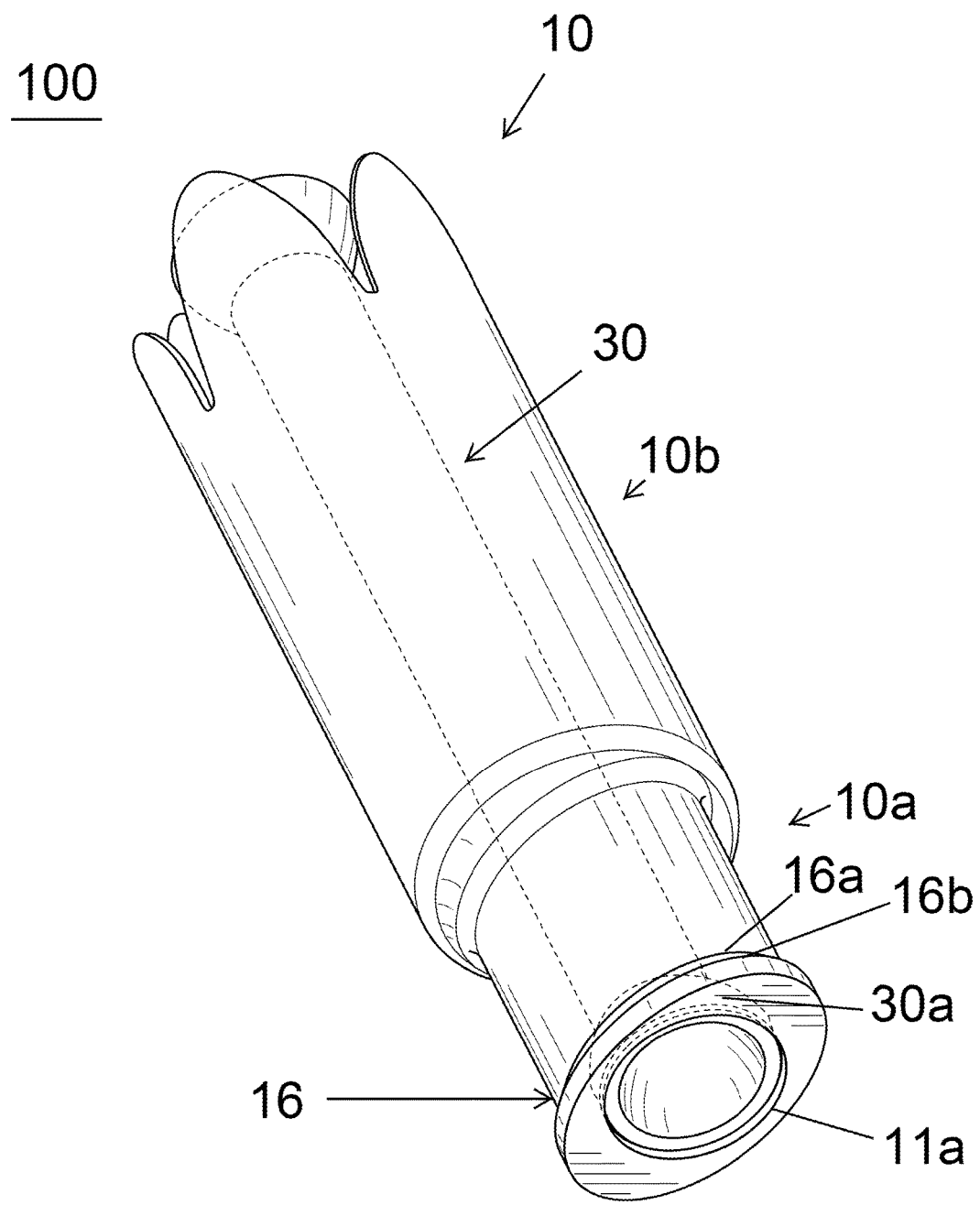
FIG. 8C is a third sequential assembly view of the tampon applicator assembly of FIG. 1.
Figure 8D:
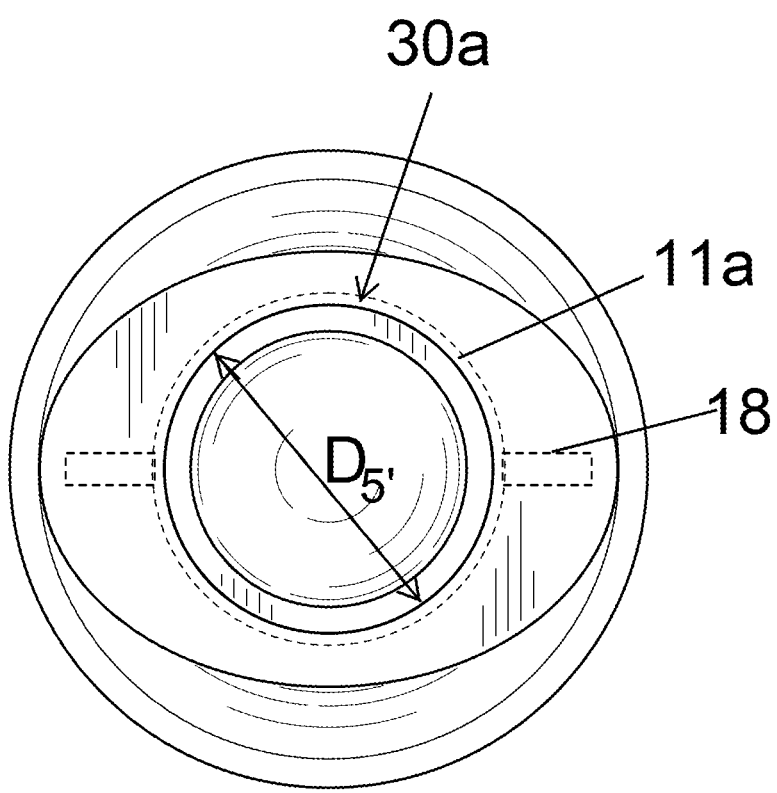
FIG. 8D is a fourth sequential assembly view of the tampon applicator assembly of FIG. 1.

Turning to FIGS. 8C and 8D, as the plunger 30 is further moved proximally through the channel 14, proximal flared end portion 30a engages the base 16b of the beveled portion 16b of wall 12. The proximal flared end portion 30a of plunger 30 is radially compressed due to the reduced diameter of the wall 12 from $D_{2b}$ to $D_{2a}$ (FIG. 7) between the base 16b and collar 16a of beveled portion 16. As the proximal flared end portion 30a of plunger 30a is compressed, proximal flared end portion 30a undergoes radial deformation such that proximal flared end portion 30a defines a smaller, deformed diameter $D_5'$ to pass through the proximal end 10a of barrel 10. Proximal flared end portion 30a undergoes radial deformation in the form of creases, folds, kinks, and/or dents, to name a few. In this regard, barrel 10 is configured to deform a portion of plunger 30 passing along beveled portion 16 of wall 12 so that the proximal flared end portion 30a passes through the narrower collar 16a and proximal end 10a of barrel 10.

Figure 8E:
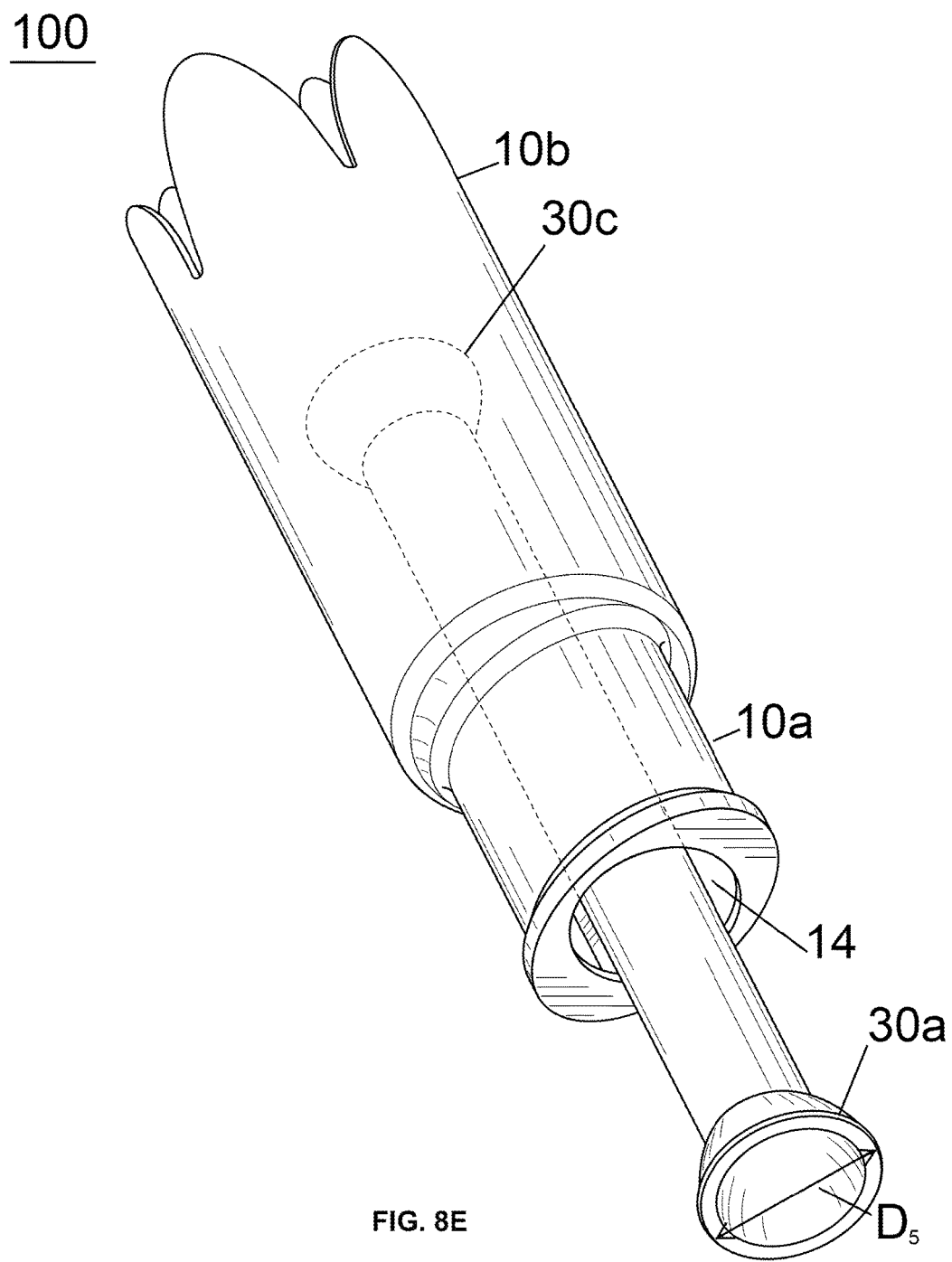
FIG. 8E is a fifth sequential assembly view of the tampon applicator assembly of FIG. 1.

Turning to FIG. 8E, as the proximal flared end portion 30a of plunger 30 passes through the proximal opening 10a of barrel 10, the proximal flared end portion 30a radially expands from the deformed diameter $D_5'$ toward its initial, larger diameter $D_5$. Once the proximal flared end portion 30a of plunger 30 has cleared the proximal opening 10a of barrel 10, plunger 30 is freely slidably within the channel 14 along the proximal portion 10a of barrel 10.

Figure 9A:
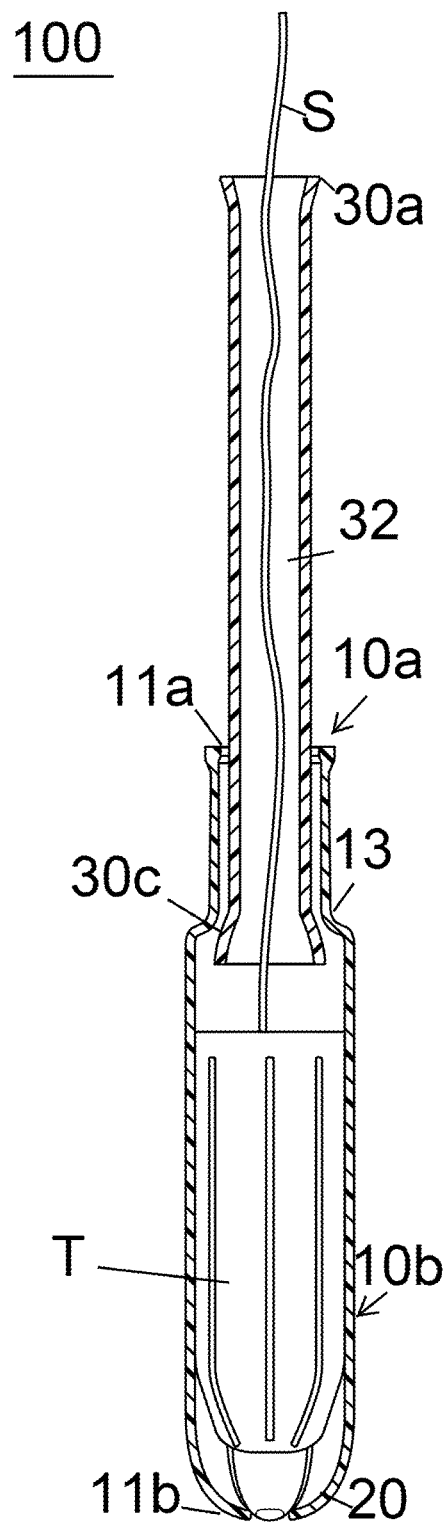
FIG. 9A is a first sequential cross-sectional view of the tampon applicator assembly of FIG. 1 assembled and loaded with a tampon.

Turning to FIG. 9A, tampon applicator assembly 100 is shown fully assembled in cross-section. A tampon T is inserted through the distal end 10b of barrel 10 so that tampon T is disposed in the distal portion 10b of barrel 10. A string S extends proximally from the tampon T through the passage 32 of plunger 30 and extends away from tampon applicator assembly 100 so that string S can be used to retrieve tampon T following use. The portion of the interior surface 12a of wall 12 along neck 13 inhibits the tampon T from moving proximally away from the distal portion 10b of barrel 10. Plunger 30 is initially positioned so that the distal flared end portion 30c is disposed proximally and/or in abutment with the tampon T. Prior to use, petals 20 are disposed in a radially inward and closed configuration so that petals 20 define a substantially closed end of barrel 10 to retain tampon T.

Figure 9B:
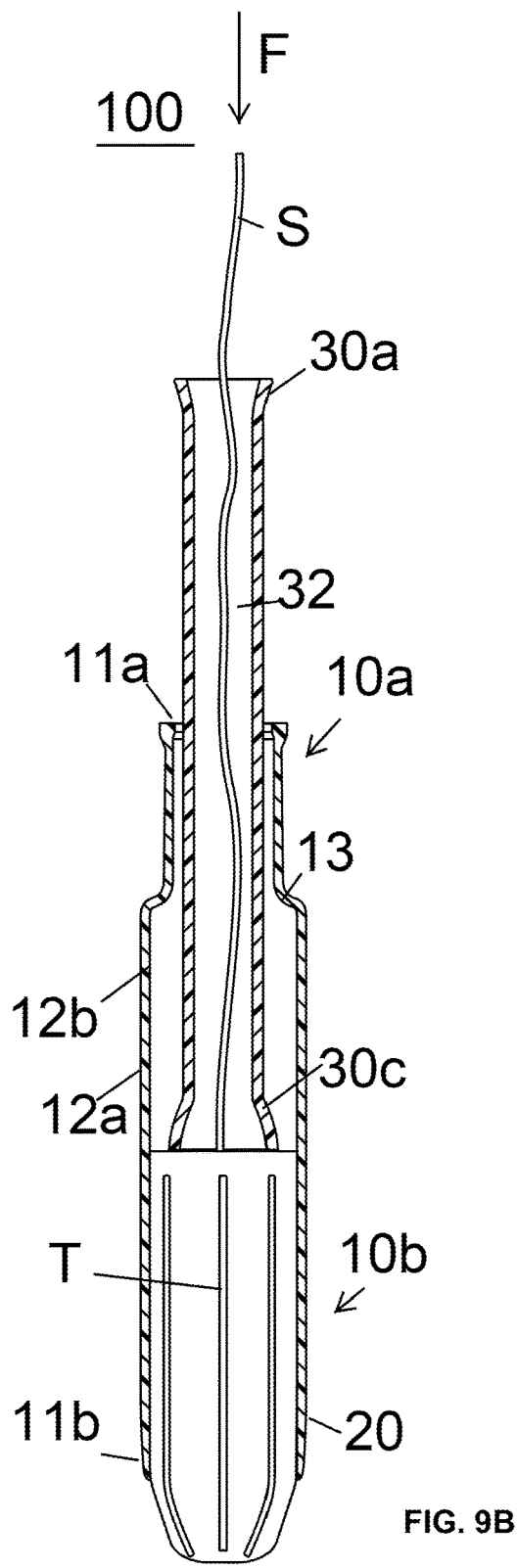
FIG. 9B is a second sequential cross-sectional view of the tampon applicator assembly FIG. 1 with the plunger pushing the tampon from the barrel.

Referring to FIG. 9B, a user exerts a force F on plunger 30 so that the distal flared end portion 30c of plunger 30 urges the tampon T toward the distal end 11b of barrel 10. Tampon T forcibly contacts the petals 20 to move from an initial, closed position to a second, open position. In this regard, the distal end 11b of barrel 10 dilates to allow tampon T to exit. As tampon T is urged from barrel 10, tampon T is frictionally engaged by the walls of the user's vaginal canal so that as applicator assembly 100 is withdrawn, tampon T remains disposed in the body cavity (not shown).

While this invention has been described in conjunction with the embodiments outlined above, it is evident that many alternatives, modifications and variations will be apparent to those skilled in the art. For example, the tampon applicator assemblies disclosed herein may include any number of surface designs or patterns for aesthetic effect. Accordingly, the exemplary embodiments of the invention, as set forth above, are intended to be illustrative, not limiting. Various changes may be made without departing from the spirit and scope of the invention.

The invention claimed is:

1. A tampon applicator assembly, comprising:
   a barrel comprising:
   a proximal opening;
   a distal opening; and
   a wall with an interior surface that defines a channel extending from the proximal opening to the distal opening, the wall comprising a first narrowing portion having a diameter narrower than a distal portion of the channel and comprising a beveled portion which comprises the proximal opening, the channel configured to releasably retain a tampon, wherein the beveled portion has a minimum diameter, and has an internal diameter narrower than an internal diameter of the distal portion of the channel and of the narrowing portion, and wherein the internal diameter of a proximal portion of the beveled portion is narrower than an internal diameter of a distal portion of the beveled portion and where the beveled portion is beveled inward to form the proximal opening; and a plunger disposed in the barrel and configured for slidable passage through the channel of the barrel, wherein the plunger includes a flared proximal end portion which is deformable, wherein the minimum diameter of the beveled portion is less than a diameter of a proximal portion of the plunger but wherein a minimum diameter of the narrowing portion is not less than a diameter of a proximal portion of the plunger; and wherein the plunger is so disposed that the flared proximal end portion of the plunger is outside of the proximal opening of the barrel and a flared distal end of the plunger is within the barrel.

2. The tampon applicator assembly of claim 1, wherein at least a pair of internal ridges extends along the interior surface of the wall into the channel.

3. The tampon applicator assembly of claim 2, wherein the pair of internal ridges is configured to align the plunger with the channel as the plunger slides through the channel.

4. The tampon applicator assembly of claim 3, wherein the pair of internal ridges is disposed along an elliptical proximal portion of the barrel defining a major diameter and a minor diameter.

5. The tampon applicator assembly of claim 4, wherein the pair of internal ridges extend along the major diameter of the elliptical proximal portion.

6. The tampon applicator assembly of claim 5, wherein the pair of internal ridges defines a diameter therebetween that is greater than or equal to the minor diameter of the channel.

7. The tampon applicator assembly of claim 2, wherein the pair of interior ridges is spaced from the beveled portion.

8. The tampon applicator assembly of claim 1, wherein the beveled portion has a greater rigidity than a rigidity of the proximal portion of the plunger.

9. The tampon applicator assembly of claim 1, wherein the beveled portion comprises a base defining a maximum diameter of the beveled portion and a collar defining the minimum diameter of the beveled portion.

10. The tampon applicator assembly of claim 1, wherein the proximal opening is circular.

11. The tampon applicator assembly of claim 1, wherein the proximal opening includes one or more cutouts extending away from the channel.

12. The tampon applicator assembly of claim 11, wherein the proximal opening includes two pairs of diametrically opposed cutouts extending away from the channel.

13. The tampon applicator assembly of claim 12, wherein each of the cutouts is semi-circular.

14. A method of assembling a tampon applicator assembly, comprising:

providing a tampon applicator assembly comprising:
a barrel that comprises a proximal opening, a distal opening, and a wall with an interior surface that defines a channel extending from the proximal opening to the distal opening, the wall comprising a first narrowing portion having a diameter narrower than a distal portion of the channel and comprising a beveled portion which comprises the proximal opening, wherein the beveled portion has an internal diameter narrower than an internal diameter of the distal portion of the channel and of the narrowing portion, and wherein the internal diameter of a proximal portion of the beveled portion is narrower than an internal diameter of a distal portion of the beveled portion and where the beveled portion is beveled inward to form the proximal opening; and a plunger disposed in the barrel and configured for slidable passage through the channel of the barrel, wherein the plunger includes a flared proximal end portion which is deformable, wherein a minimum diameter of the beveled portion is less than a diameter of a proximal portion of the plunger;

inserting the plunger into the distal opening of the barrel and proximally through the channel toward the beveled portion; and moving the plunger along the beveled portion so that a portion of the plunger is deformed by the beveled portion and then moving the plunger through the proximal opening of the barrel so that the deformed portion of the plunger resiliently returns to an unstressed resting configuration and the plunger is so disposed that the flared proximal end portion of the plunger is outside of the proximal opening of the barrel and a flared distal end of the plunger is within the barrel.

* * * * *